United States Patent
Benz et al.

(10) Patent No.: US 12,404,490 B2
(45) Date of Patent: Sep. 2, 2025

(54) AGGF1 IMMUNOGENIC COMPOSITIONS

(71) Applicant: Nantomics LLC, Culver City, CA (US)

(72) Inventors: Stephen Charles Benz, Culver City, CA (US); Andrew Nguyen, Culver City, CA (US); Charles Joseph Vaske, Culver City, CA (US); John Zachary Sanborn, Culver City, CA (US)

(73) Assignee: NantOmics LLC, Culver City, CA (US)

(*) Notice: Subject to any disclaimer, the term of this patent is extended or adjusted under 35 U.S.C. 154(b) by 109 days.

(21) Appl. No.: 17/938,270

(22) Filed: Oct. 5, 2022

(65) Prior Publication Data
US 2023/0210969 A1 Jul. 6, 2023

Related U.S. Application Data

(63) Continuation of application No. 16/571,008, filed on Sep. 13, 2019, now Pat. No. 11,504,420, which is a continuation of application No. 15/565,203, filed as application No. PCT/US2016/026798 on Apr. 8, 2016, now abandoned.

(60) Provisional application No. 62/144,745, filed on Apr. 8, 2015.

(51) Int. Cl.
| | |
|---|---|
| *A61K 47/68* | (2017.01) |
| *A61K 39/00* | (2006.01) |
| *C07K 14/47* | (2006.01) |
| *C07K 16/22* | (2006.01) |
| *C07K 16/30* | (2006.01) |
| *C12N 5/0783* | (2010.01) |
| *C12N 5/09* | (2010.01) |
| *G01N 33/574* | (2006.01) |

(52) U.S. Cl.
CPC .... *C12N 5/0638* (2013.01); *A61K 39/001102* (2018.08); *A61K 39/001144* (2018.08); *A61K 47/6851* (2017.08); *C07K 14/4702* (2013.01); *C07K 16/22* (2013.01); *C07K 16/30* (2013.01); *C12N 5/0646* (2013.01); *C12N 5/0693* (2013.01); *G01N 33/57407* (2013.01); *A61K 2039/505* (2013.01); *A61K 2039/53* (2013.01); *A61K 2039/80* (2018.08); *A61K 2039/812* (2018.08); *A61K 2039/892* (2018.08); *C07K 2317/34* (2013.01); *C07K 2319/55* (2013.01); *C07K 2319/60* (2013.01)

(58) Field of Classification Search
None
See application file for complete search history.

(56) References Cited

U.S. PATENT DOCUMENTS

| | | | |
|---|---|---|---|
| 8,207,315 B2 * | 6/2012 | Wang | C07K 14/515 536/23.1 |
| 8,652,473 B2 | 2/2014 | Johns et al. | |
| 11,504,420 B2 | 11/2022 | Benz et al. | |
| 2005/0048070 A1 | 3/2005 | Ditzel et al. | |
| 2011/0293637 A1 | 12/2011 | Hacohen et al. | |

FOREIGN PATENT DOCUMENTS

| | | |
|---|---|---|
| EP | 2279749 A1 | 2/2011 |
| WO | 2011143656 A2 | 11/2011 |
| WO | 2015103037 A2 | 7/2015 |
| WO | 2015191666 A2 | 12/2015 |

OTHER PUBLICATIONS

Wang et al (Med Oncol. 2015, 32:131, online publication Mar. 22, 2015).*
Tian et al (Nature, 2004, 427, 640-645).*
Office Action received in Canadian Patent Application Serial No. 2987730 dated Sep. 17, 2019, 4 pages.
Fritsch, et al., "HLA-Binding Properties of Tumor Neoepitopes In Humans," Cancer Immunology Research, Jun. 2014, vol. 2, No. 6, pp. 522-529.
First Office Action received for Canadian Patent Application Serial No. 2987730 dated Jul. 31, 2018, 06 pages.
Second Office Action received for Canadian Patent Application Serial No. 2987730 dated Feb. 25, 2019, 04 pages.
Haisma H.J, "Monoclonal antibodies and cancer: Studies on the use of monoclonal antibodies for imaging and therapy of cancer, with a special emphasis on ovarian carcinoma", Dec. 8, 1957, 175 pages.
Gubin et al., Tumor neoantigens: building a framework for, personalized cancer immunotherapy, The Journal of Clinical Investigation, Sep. 2015, vol. 125, No. 9, pp. 3413-3421.
Srivastava P.K, "Neoepitopes of Cancers: Looking Back, Looking Ahead", Cancer Immunology Research, Sep. 1, 2015, vol. 3, No. 9, pp. 969-977.
Monteiro J, "Cancer Immunotherapy Scores Again", Cell, Jan. 15, 2015, vol. 160, pp. 7-9.
Hundal et al., "pVAC-Seq: A genome-guided in silico approach to identifying tumor neoantigens", Genome Medicine, Jan. 29, 2016, vol. 8, No. 11, pp. 1-11.

(Continued)

*Primary Examiner* — Laura B Goddard
(74) *Attorney, Agent, or Firm* — Umberg Zipser LLP; Martin Fessenmaier; Priti Phukan

(57) ABSTRACT

Certain universal neoepitopes and cancer specific neoepitopes and methods therefor are presented that may be used in immunotherapy and cancer diagnosis. Preferred therapeutic and diagnostic compositions include antibodies or fragments thereof that bind to neoepitopes on cancer cells.

14 Claims, No Drawings

Specification includes a Sequence Listing.

(56) References Cited

OTHER PUBLICATIONS

Akkawi et al., "The human VG5Q gene 2 transcript is overexpressed in colorectal and bladder carcinomas", Gene Therapy Molecular Biology, 2006, vol. 10, pp. 173-178.
Supplementary European Search report received for European Patent Application Serial No. 16777432.2 dated Aug. 29, 2018, 03 pages.
International Preliminary Report on Patentability received for PCT Application Serial No. PCT/US2016/026798 dated Oct. 10, 2017, 01 pages.
ISA/KR, International Search Report and Written Opinion, completed Jul. 18, 2016 for PCT Application No. PCT/US2016/026798, 14 pages.
Lutz, et al., "Can we predict mutant neoepitopes in human cancers for patient-specific vaccine therapy?" Cancer Immunology Research, vol. 2, No. 6, pp. 518-521 (Jun. 2014).
Notice of Allowance received for Canadian Patent Application Serial No. 2987730 dated Dec. 10, 2019.
Fritsch, et al., "Personal neoantigen cancer vaccines," OncoImmunology, vol. 3, Article No. e29311, Internal pp. 1-3 (Jun. 2014).
Sykulev et al., "Evidence that a Single Peptide—MHC Complex on a Target Cell Can Elicit a Cytolytic T Cell Response", Immunity, Jun. 1, 1996, vol. 4, No. 6, pp. 565-571.
Extended European Search report received for European Patent Application Serial No. 16777432.2 dated Nov. 30, 2018, 11 pages.
Summons to attend oral proceedings pursuant to Rule 115(1) EPC received for European Patent Application Serial No. 16777432.2 dated Aug. 23, 2019, 5 pages.

* cited by examiner

AGGF1 IMMUNOGENIC COMPOSITIONS

This application is a continuation application of allowed US application with the Ser. No. 16/571,008, filed Sep. 13, 2019, which is a continuation of US application with the Ser. No. 15/565,203, filed Oct. 9, 2017, which is a national stage application of PCT/US2016/026798, filed Apr. 8, 2016, which claims priority to U.S. provisional application Ser. No. 62/144,745, filed Apr. 8, 2015, all of which are incorporated by reference herein.

SEQUENCE LISTING XML

The content of the following file which was electronically submitted via EFS-Web along with the present application is incorporated by reference herein in its entirety: a computer readable form (CRF) of the Sequence Listing, file name: 102402_0011US-CON2.xml, created on Oct. 5, 2022, and having the size 92 KB.

FIELD OF THE INVENTION

The field of the invention is methods and compositions for cancer neoepitopes, especially as it relates to neoepitopes common to certain cancers.

BACKGROUND

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Random mutations in tumor cells can give rise to unique tumor specific antigens (i.e., cancer neoepitopes or neoepitopes). As such, and at least conceptually, neoepitopes may thus provide a unique precision target for immunotherapy. Additionally, it has been shown that cytolytic T-cell responses can be triggered by very small quantities of peptides (e.g., Sykulev et al., *Immunity*, Volume 4, Issue 6, p 565-5'71, 1 Jun. 1996). In view of these findings, the identification of cancer neoepitopes as therapeutic targets has attracted much attention. Unfortunately, current data tend to support the notion that all or almost all cancer neoepitopes are unique to a patient and specific tumor and therefore fail to provide any useful guidance for development of an immunotherapeutic agent suitable for more than one patient and tumor type (see e.g., Fritsch et al. *Cancer Immunol Res;* 2(6); 1-8). Moreover, as a proper immune reaction is also at least to some degree dependent on a patient's HLA type, development of a 'broad spectrum' immunotherapeutic targeting single neoepitopes has been deemed unlikely as two factors with high variability (neoepitope sequence and HLA-type) must be met.

Thus, even though neoepitopes in tumors can be predicted relatively easily, there is still a need to provide improved compositions and methods for cancer epitopes and their use in the diagnosis and treatment of neoplastic diseases.

SUMMARY OF THE INVENTION

The inventive subject matter is directed to various compositions and methods related to cancer neoepitopes that occur across a variety of different cancers or different subtypes of cancers. In at least some aspects, such cancer neoepitopes also bind to various distinct HLA types and as such may be used as cancer immunotherapeutic agents for multiple and distinct patients. Therefore, and viewed form a different perspective, the inventors discovered various conserved neoepitopes that have a sequence and that occur at a frequency that allows for manufacture of immunotherapeutic compositions for the diagnosis or treatment of cancer or specific cancer types in a significant subpopulation of patients expressing such neoepitopes.

In one aspect of the inventive subject matter, the inventors contemplate a method of directing an agent to a cancer cell that includes a step of contacting the cancer cell (preferably in vivo) with an antibody or antibody fragment that binds to a cancer neoepitope in an AGGF1 (angiogenic factor with g-patch and FHA domains 1) protein, wherein the cancer neoepitope is formed by a V202L mutation in the AGGF1 protein. In such contemplated methods the cancer cell may be a BRCA (breast cancer) cell, a CESC (cervical squamous cell carcinoma) cell, a HNSC (head and neck squamous cell carcinoma) cell, a LIHC (liver hepatocellular carcinoma) cell, a LUAD (lung adenocarcinoma) cell, a LUSC (lung squamous cell carcinoma) cell, an OV (ovarian cancer) cell, a READ (renal adenocarcinoma) cell, a STAD (stomach adenocarcinoma) cell, a THCA (thyroid carcinoma) cell, or a UCEC (uterine corpus endometrioid carcinoma) cell.

Moreover, it is contemplated that the antibody or antibody fragment may be synthetic or may comprise an IgG or other type of antibody, a Fab, a F(ab')$_2$, or a scFv, each of which may or may not be further coupled to a therapeutic agent, a radiologic agent, or an imaging agent. Where desired, the antibody or fragment thereof may also be coupled to a portion of a T-cell receptor, and/or may be coupled to a cytotoxic T-cell or an NK cell. Depending on the type of antibody, it is contemplated that the antibody or fragment thereof may be produced in a process that includes a step of immunizing a mammal with a peptide having SEQ ID NO:1, SEQ ID NO:2, or SEQ ID NO:3. Therefore, it should be noted that the cancer neoepitope may have a sequence of SEQ ID NO:1, SEQ ID NO:2, or SEQ ID NO:3.

Therefore, the inventors also contemplate the use of an antibody or fragment thereof to direct a diagnostic or therapeutic agent to a cancer cell, wherein the antibody or fragment thereof binds to a cancer neoepitope in an AGGF1 protein, and wherein the cancer neoepitope is formed by a V202L mutation in the AGGF1 protein. Most typically, the cancer cell will be selected form the group consisting of a BRCA (breast cancer) cell, a CESC (cervical squamous cell carcinoma) cell, a HNSC (head and neck squamous cell carcinoma) cell, a LIHC (liver hepatocellular carcinoma) cell, a LUAD (lung adenocarcinoma) cell, a LUSC (lung squamous cell carcinoma) cell, an OV (ovarian cancer) cell, a READ (renal adenocarcinoma) cell, a STAD (stomach adenocarcinoma) cell, a THCA (thyroid carcinoma) cell, and a UCEC (uterine corpus endometrioid carcinoma) cell. As noted before, it is contemplated that the diagnostic or therapeutic agent may comprise a radiologic agent, an imaging agent, a portion of a T-cell receptor, a cytotoxic T-cell, an NK cell, or that the therapeutic agent is the antibody.

Viewed form a different perspective, the inventors also contemplate an antibody or fragment thereof that binds to a cancer neoepitope in an AGGF1 protein, wherein the cancer neoepitope is formed by a V202L mutation in the AGGF1 protein, and wherein the cancer neoepitope has a sequence of SEQ ID NO:1, SEQ ID NO:2, or SEQ ID NO:3. In at least some aspects, the antibody may be an IgG antibody or may further comprise a portion of a T-cell receptor, or may be configured as a scFv. As before, it is contemplated that the antibody or fragment thereof may further comprise a therapeutic or diagnostic agent.

Consequently, the inventors also contemplate an immunologic composition that includes a carrier to which a peptide is coupled that has a sequence of SEQ ID NO:1, SEQ ID NO:2, or SEQ ID NO:3, wherein the composition is formulated as a vaccine. Where desired, the peptide may also be further coupled to at least one additional cancer neoepitope peptide.

In other aspects of the inventive subject matter, the inventors also contemplate a recombinant nucleic acid that includes a promoter operably coupled to a sequence encoding a protein having a sequence of SEQ ID NO:1, SEQ ID NO:2, or SEQ ID NO:3. For example, especially preferred recombinant nucleic acids include viral or bacterial expression vectors. Where desired, the recombinant nucleic acid may further comprise at least one additional sequence that encodes at least one additional cancer neoepitope peptide.

In still further aspects of the inventive subject matter, the inventors also contemplate a method of directing an agent to a breast cancer cell that includes a step of contacting (e.g., in vivo) the cancer cell with an antibody or fragment thereof that binds to a cancer neoepitope having a sequence of any one of SEQ ID NO:4 to SEQ ID NO:28, of any one of SEQ ID NO:29 to SEQ ID NO:53, of any one of SEQ ID NO:54 to SEQ ID NO:78, or of any one of SEQ ID NO:79 to SEQ ID NO:103.

For example, where the cancer cell is a triple negative breast cancer cell, the neoepitope may have a sequence of any one of SEQ ID NO:4 to SEQ ID NO:28, or where the cancer cell is a ER (estrogen receptor) positive breast cancer cell, the neoepitope may have a sequence of any one of SEQ ID NO:29 to SEQ ID NO:53, or where the cancer cell is a PR (progesterone receptor) positive breast cancer cell, the neoepitope may have a sequence of any one of SEQ ID NO:54 to SEQ ID NO:78, or where the cancer cell is a HER2 (human epidermal growth factor receptor 2) positive breast cancer cell, and wherein the neoepitope has a sequence of any one of SEQ ID NO:79 to SEQ ID NO:103.

While not limiting the inventive subject matter, it is contemplated that the antibody or fragment thereof may comprise an IgG antibody, a Fab, a F(ab')2, and a scFv, and/or that the antibody or fragment thereof may further comprise a therapeutic agent, an imaging agent, or a radiologic agent. In other examples, the antibody or fragment thereof may also be coupled to a portion of a T-cell receptor, or may be coupled to a cytotoxic T-cell or an NK cell. It should also be appreciated that the antibody or fragment thereof may be produced in a process that includes a step of immunizing a mammal with any one of a peptide having SEQ ID NO:4 to SEQ ID NO:103.

Consequently, the inventors also contemplate the use an antibody or fragment thereof to direct a diagnostic or therapeutic agent to a cancer cell, wherein the antibody or fragment thereof binds to a cancer neoepitope having a sequence of any one of SEQ ID NO:4 to SEQ ID NO:28, of any one of SEQ ID NO:29 to SEQ ID NO:53, of any one of SEQ ID NO:54 to SEQ ID NO:78, or of any one of SEQ ID NO:79 to SEQ ID NO:103. In preferred uses, the cancer cell is a triple negative breast cancer cell, and the neoepitope has a sequence of any one of SEQ ID NO:4 to SEQ ID NO:28, or the cancer cell is a ER (estrogen receptor) positive breast cancer cell, and the neoepitope has a sequence of any one of SEQ ID NO:29 to SEQ ID NO:53, or the cancer cell is a PR (progesterone receptor) positive breast cancer cell, and the neoepitope has a sequence of any one of SEQ ID NO:54 to SEQ ID NO:78, or the cancer cell is a HER2 (human epidermal growth factor receptor 2) positive breast cancer cell, and the neoepitope has a sequence of any one of SEQ ID NO:79 to SEQ ID NO:103. In further preferred uses, the diagnostic or therapeutic agent may comprise a radiologic agent, an imaging agent, a portion of a T-cell receptor, a cytotoxic T-cell, or an NK cell, or therapeutic agent may be the antibody (e.g., in form of an IgG).

Viewed from another perspective, the inventors therefore also contemplate an antibody or fragment thereof that binds to a cancer neoepitope having a sequence of any one of SEQ ID NO:4 to SEQ ID NO:28, of any one of SEQ ID NO:29 to SEQ ID NO:53, of any one of SEQ ID NO:54 to SEQ ID NO:78, or of any one of SEQ ID NO:79 to SEQ ID NO:103. Such antibodies or fragments may be an IgG or may further comprises a portion of a T-cell receptor, or may be configured as a scFv, and/or may further comprise a therapeutic or diagnostic agent.

In still further aspects of the inventive subject matter, the inventors also contemplate an immunologic composition that includes a carrier to which is coupled a peptide having a sequence of any one of SEQ ID NO:4 to SEQ ID NO:28, of any one of SEQ ID NO:29 to SEQ ID NO:53, of any one of SEQ ID NO:54 to SEQ ID NO:78, or of any one of SEQ ID NO:79 to SEQ ID NO:103, wherein the composition is formulated as a vaccine. Where desired, the peptide may be further coupled to at least one additional cancer neoepitope peptide.

On the other hand, the inventors also contemplate a recombinant nucleic acid that comprises a promoter operably coupled to a sequence that encodes a protein having a sequence of any one of SEQ ID NO:4 to SEQ ID NO:28, of any one of SEQ ID NO:29 to SEQ ID NO:53, of any one of SEQ ID NO:54 to SEQ ID NO:78, or of any one of SEQ ID NO:79 to SEQ ID NO:103. Most preferably, the recombinant nucleic acid is a viral expression vector, and/or may further comprises at least one additional sequence that encodes at least one additional cancer neoepitope peptide.

Various objects, features, aspects and advantages of the inventive subject matter will become more apparent from the following detailed description of preferred embodiments.

DETAILED DESCRIPTION

The inventors have discovered neoepitopes that are common among a subpopulation of cancer patients diagnosed with a relatively wide spectrum of cancers (e.g., breast cancer, cervical squamous cell carcinoma, head and neck squamous cell carcinoma, lung squamous cell carcinoma, liver hepatocellular carcinoma, lung adenocarcinoma, ovarian cancer, renal adenocarcinoma, stomach adenocarcinoma, thyroid carcinoma, uterine corpus endometrioid carcinoma, etc.), or subpopulation of a group of cancer types (e.g., triple negative breast cancer, ER positive breast cancer cell, PR positive breast cancer, HER2 positive breast cancer).

More specifically, and with respect to discovery of neoepitopes contemplated and/or presented herein, preferred methods will include a step of performing an omics analysis. Most typically, the omics analysis will be at least a whole genome sequencing, or an exome sequencing of the patient's genome, preferably in conjunction with a matched normal (non-diseased) sample of the same patient. There are numerous such methods known in the art, and specific suitable examples for omics analysis are described in US20120059670A1 and US20120066001A1, which are incorporated by reference herein. It should therefore be appreciated that not only cancer specific mutations can be readily detected, but that such information is also specific to a particular patient. Additionally, it is generally preferred that the omics analysis also includes an analysis of gene expression (transcriptomic analysis) to so help identify the level of expression for the gene with a mutation. Viewed from another perspective, transcriptomic analysis may be suitable, alone or in combination with genomic analysis, to identify and quantify genes having a cancer and patient specific mutation. There are numerous methods of transcriptomic analysis known in the art, and all of the known methods are deemed suitable for use herein. For example, and among other choices, quantitative PCR or hybridization techniques and in silico determination of relative frequency are contemplated. Taken the above into consideration, it should therefore be appreciated that a patient sample comprising DNA and RNA from tumor and matched normal tissue can be used to identify specific mutations and to quantify such mutations.

Of course, it should also be appreciated that further downstream analysis may be performed on the so identified sequence differences to identify those that lead to a new peptide sequence based on the cancer and patient specific mutation. In other words, silent mutations may be eliminated from the list of identified neoepitopes. Neoepitopes may therefore be identified by considering the type (e.g., deletion, insertion, transversion, transition, translocation) and impact of the mutation (e.g., non-sense, missense, frame shift, etc.), and may as such serve as a first content filter through which silent and other non-relevant (e.g., non-expressed) mutations are eliminated. It should further be appreciated that neoepitope sequences can be defined as sequence stretches with relatively short length (e.g., 7-11 mers) wherein such stretches will include the change(s) in the amino acid sequences. Most typically, the changed amino acid will be at or near the central amino acid position. For example, a typical neoepitope may have the structure of A4-N-A4, or A3-N-A5, or A2-N-A7, or A5-N-A3, or A7-N-A2, where A is an amino acid and N is a changed amino acid (relative to wild type or matched normal)

The so obtained neoepitopes may then be subject to further detailed analysis and filtering using predefined structural and expression parameters, and/or sub-cellular location parameters. For example, it should be appreciated that neoepitope sequences are only retained provided they will meet a predefined expression threshold (e.g., at least 20%, 30%, 40%, 50%, or higher expression of matched normal or average/reference value for healthy tissue) and/or are identified as having a membrane associated location (e.g., are located at the outside of a cell membrane of a cell). Further contemplated analyses may include structural calculations that delineate whether or not a neoepitope is likely to be solvent exposed, presents a structurally stable epitope, etc.

In yet another aspect of filtering, the neoepitopes may be compared against a database that contains known human sequences to so avoid use of a human-identical sequence. Moreover, filtering may also include removal of neoepitope sequences that are due to SNPs in the patient. For example, The Single Nucleotide Polymorphism Database (dbSNP) is a free public archive for genetic variation within and across different species developed and hosted by the National Center for Biotechnology Information (NCBI) in collaboration with the National Human Genome Research Institute (NHGRI). Although the name of the database implies a collection of one class of polymorphisms only (i.e., single nucleotide polymorphisms (SNPs)), it in fact contains a relatively wide range of molecular variation: (1) SNPs, (2) short deletion and insertion polymorphisms (indels/DIPs), (3) microsatellite markers or short tandem repeats (STRs), (4) multinucleotide polymorphisms (MNPs), (5) heterozygous sequences, and (6) named variants. The dbSNP accepts apparently neutral polymorphisms, polymorphisms corresponding to known phenotypes, and regions of no variation. Using such database, the patient and tumor specific neoepitopes may be further filtered to remove those know sequences, yielding a therapeutic sequence set with a plurality of neoepitope sequences.

As preferred neoepitopes will be employed in immunotherapy, the neoepitopes are at least in some aspects of the inventive subject matter further filtered by their ability to bind to an HLA type, and most typically to an HLA type of one or more patients. Thus, contemplated methods and compositions will include HLA binding prediction or the use of HLA-matched neoepitopes. There are numerous manners of determining a person's HLA type, and all manners including conventional laboratory methods (e.g., sequence-specific oligonucleotide probe hybridization, PCR amplification with sequence-specific primers, Sanger sequencing, or sero-typing . . . ) and in silico methods (e.g., from RNA reads as described in Genome Med. 2013, 4 (12): 102- or PLoS One. 2013, 8 (6): e67885-, or from DNA reads as described in Genome Med. 2012, 4 (12): 95- or Nucleic Acids Res. 2013, 41 (14): e142-, or BMC Genomics 2014, 15:325) are deemed suitable for use herein. Most typically, HLA binding is considered strong for (calculated) Kd values of <50 nM, while binding is considered moderate for (calculated) Kd values of <500 nM.

Therefore, neoepitopes can be scored/ranked based on allele frequency multiplied by the transcripts per million number to get a likelihood score. This score can then be further augmented using HLA information and calculated or actual binding affinity to the patient's HLA type. For example, an exemplary ranking format may be:
>254 NM_001000.3 RPL39 Missense p.M29K A->T Normal: WIRMKTGNK, AF: 0.179104477612 TPM: 1023.96 TPM MEDIAN: 7.35 LL: 183.395820896 netMHC: 242.96 Allele: HLA-A0301 WIRKKTGNK.

Here, the file is a FASTA formatted file, and entries start with the '>' character, which just reports sample information. The next line is the neoepitope. In the sample information line contains a number used for indexing the sample (e.g., 254), the Refseq Gene ID (e.g., NM_001000.3), the HUGO common name (e.g., RPL39), the variant classification (e.g., Missense), the protein change (e.g., p.M29K), the base pair change (e.g., A->T), the normal epitope (e.g., Normal: WIRMKTGNK), allele frequency (e.g., AF: 0.179104477612), Transcripts per million for this gene (e.g., TPM: 1023.96), TPM MEDIAN which is the median expression level of all the genes (e.g., TPM MEDIAN: 7.35), the LL score which is just AF×TPM (e.g., LL: 183.395820896), the netMHC predicted binding value (e.g., netMHC: 242.96), and the specific HLA allele that the neoepitope binds to (e.g., Allele: HLA-A0301). The next line is then the neoepitope (e.g., WIRKKTGNK).

Therefore, neoepitopes suitable for use herein may be identified in a process that uses incremental synchronous alignment of tumor and matched normal BAM (or SAM or GAR) files to so identify differences genuine to the tumor and specific to the patient. Most typically the differences are recorded in VCF format and identified neoepitopes are further processed as discussed above to select for (highly, at least 50% of normal) expressed neoepitopes that bind with an at least moderate, and more preferably strong affinity to the patient's HLA type. Of course, it should be appreciated that the so obtained list of filtered neoepitopes is further compared to known epitopes (of the same patient) to avoid to selection of naturally occurring sequences.

Notably, and as further described in more detail below, the inventors conducted large scale analyses of known tumor and matched normal sequences in omics databases and were able to identify several neoepitopes that occurred in a subpopulation of patients diagnosed with various cancers, and that occurred in cancer sub-types of patients diagnosed with breast cancer.

EXAMPLES

Based on the ever increasing number in available omics data, the inventors queried publicly available databases whether or not universal cancer neoepitopes could exist. To that end, the inventors reviewed the TCGA data sets in an effort to identify recurrent neoepitopes in cancers, and to so potentially provide an avenue to universal or cancer specific immune therapeutic agents. Table 1 below lists TCGA data sets (whole genome sequencing), with the relevant cancer subtypes and epitope information found within these data sets.

TABLE 1

| Cancer | Total Samples | Total Epitope | Unique Epitope/Sample | Total Epitope/Sample | Average Coding Variant Count | Highest Repeat Epitope Across Samples | Max Recurrent/Total Sample |
|---|---|---|---|---|---|---|---|
| BLCA | 23 | 35781 | 1555 | 1583 | 180 | 4 | 0.17 |
| BRCA | 98 | 69791 | 712 | 736 | 86 | 12 | 0.12 |
| CESC | 16 | 11662 | 728 | 763 | 86 | 2 | 0.13 |
| COAD | 46 | 334807 | 7321 | 7538 | 816 | 9 | 0.20 |
| DLBC | 7 | 7491 | 1070 | 1110 | 125 | 4 | 0.57 |
| GBM | 27 | 8551 | 316 | 334 | 50 | 3 | 0.11 |
| HNSC | 50 | 57154 | 1143 | 1179 | 135 | 9 | 0.18 |
| KICH | 49 | 13994 | 285 | 317 | 36 | 4 | 0.08 |
| KIRC | 40 | 20892 | 522 | 548 | 59 | 4 | 0.10 |
| KIRP | 14 | 8540 | 610 | 652 | 68 | 2 | 0.14 |
| LAML | 4 | 112 | 28 | 39 | 21 | 1 | 0.25 |
| LGG | 13 | 2803 | 215 | 230 | 24 | 10 | 0.77 |
| LIHC | 46 | 33794 | 734 | 774 | 89 | 4 | 0.09 |
| LUAD | 45 | 75651 | 1681 | 1716 | 193 | 6 | 0.13 |
| LUSC | 39 | 87087 | 2233 | 2285 | 262 | 5 | 0.13 |
| OV | 48 | 27551 | 573 | 639 | 72 | 7 | 0.15 |
| PRAD | 20 | 3031 | 151 | 212 | 22 | 2 | 0.10 |
| READ | 16 | 105482 | 6592 | 6592 | 6679 | 4 | 0.25 |
| SARC | 17 | 7686 | 452 | 474 | 54 | 1 | 0.06 |
| SKCM | 39 | 175792 | 4507 | 4583 | 535 | 11 | 0.28 |
| STAD | 29 | 112816 | 3890 | 4086 | 387 | 5 | 0.17 |
| THCA | 45 | 6266 | 139 | 164 | 19 | 9 | 0.20 |
| UCEC | 44 | 199995 | 4545 | 4690 | 503 | 8 | 0.18 |
| Average | 33.69 | 61162.13 | 1739.21 | 1793.21 | 456.56 | 5.47 | 0.16 |

Notably, the number of epitopes per tumor sample was relatively high, ranging from about 160 (for THCA) to about 6,500 (for READ). Even more notable was the fact that almost all of the epitopes found in a sample were unique epitopes, which at least at first glance seemed to contradict the possibility of shared or common cancer neoepitopes within a cancer type or among two or more cancer types. Interestingly, the fraction of coding variants produced by the neoepitopes was relatively low (at approximately 10% of total neoepitopes), but across all tumor types shared or common cancer neoepitopes nevertheless existed. For example, a single recurrent mutation was shared among about 17% of patients within a cancer subtype (BLCA data set has a single missense mutation in FGFR3 that is present in 4 out of 23 patients).

When considering common or shared neoepitopes across cancers in the TCGA data set, the inventors noted that the highest single recurrent mutation was shared between 3% of all patients as is shown in Table 2 below, which is unexpectedly high when considering the nature of different cancer types and difference in patients.

TABLE 2

| Cancer | Samples | Total Epitope | Unique Epitope/Sample | Total Epitope/Sample | Average Coding Variant Count | Highest Repeat Epitope Across Samples | Repeated / Total Sample |
|---|---|---|---|---|---|---|---|
| All Cancer | 775 | 1408729 | 1817 | 1878 | 208 | 27 | 0.03 |

Indeed, for the TCGA data set examined, three epitopes were detected in 26 patients out of a total of 775 patients with different cancers (as listed in Table 1). More particularly, these neoepitopes were seen in BRCA, CESC, HNSC, LIHC, LUAD, LUSC, OV, READ, STAD, THCA and UCEC, with ~25% of samples being ovarian serous cystadenocarcinoma. Table 3 below provides more information about this shared cancer neoepitope.

TABLE 3

| 9-Mer | Occurrences in TCGA WGS data set | Gene | Protein Change | Variant Classification |
|---|---|---|---|---|
| AEAALSQTG [SEQ ID NO: 1] | 26 | AGGF1 | p.V202L | Missense |
| ALSQTGFSY [SEQ ID NO: 2] | 26 | AGGF1 | p.V202L | Missense |
| EAALSQTGF [SEQ ID NO: 3] | 26 | AGGF1 | p.V202L | Missense |

As can be readily seen from Table 3, the neoepitope occurred in the same gene and had the same protein change: At position 202 a valine was replaced by a leucine, each time in the same gene AGGF1 (angiogenic factor G patch with FHA domains 1). The AGGF1 is known to encode VGSQ, (vasculogenesis gene on 5q), which promotes angiogenesis and is overexpressed in lung cancers by microarray.

It should be appreciated that according to the American Cancer Society ~1,658,370 new cancer diagnoses are expected for the year 2015. Given that the above neoepitopes will occur in about 3% of all cancers, it must be recognized that about 49,757 patients potentially carry the AGGF1 neoepitope. This prompted the inventors to investigate whether or not the above neoepitopes would have binding affinity to various relatively common HLA types, and computational analyses were performed for selected MHC-I alleles. The results are shown in Table 4 below. Notable, the neoepitope showed strong (<50 nM) calculated binding to five MHC-I alleles, and moderate (<500 nM) binding to five additional MHC-I alleles.

TABLE 4

| Mer | HLA-A*29:02 | HLA-A*30:02 | HLA-B*15:01 | HLA-B*15:02 | HLA-B*15:03 | HLA-B*15:17 | HLA-B*35:01 | HLA-B*40:02 | HLA-B*44:02 | HLA-B*45:01 |
|---|---|---|---|---|---|---|---|---|---|---|
| ALSQTGFSY [SEQ ID NO: 2] | 19 | 29 | 25 | 161 | 59 | 150 | | | | |
| EAALSQTGF [SEQ ID NO: 3] | | | | | | 432 | 329 | | | |
| AEAALSQTG [SEQ ID NO: 1] | | | | | | | | 399 | 67 | 36 |

When considering HLA frequency for specific HLA types over the entire population, the inventors discovered that HLAs that bind to the AGGF1 neoepitopes occur in significant fractions of the US population as shown in Table 5 below (EUR: European ethnicity; AFA: African American ethnicity; API: Asia-Pacific ethnicity; HIS: Hispanic ethnicity).

TABLE 5

|  | EUR Frequency | EUR Rank | AFA Freq | AFA Rank | API Freq | API Rank | HIS Freq | HIS Rank |
|---|---|---|---|---|---|---|---|---|
| HLA-A*29:02, | 0.03279 | 6 | 0.03640 | 12 | 0.00141 | 30 | 0.04167 | 8 |
| HLA-A*30:02, | 0.00921 | 15 | 0.06219 | 6 | 0.00056 | 40 | 0.02811 | 12 |
| HLA-B*15:01, | 0.06654 | 4 | 0.00975 | 23 | 0.03480 | 11 | 0.02876 | 10 |
| HLA-B*15:02, | 0.00000 | NA | 0.00083 | 55 | 0.03565 | 10 | 0.00025 | 99 |
| HLA-B*15:03, | 0.00089 | 39 | 0.06245 | 4 | 0.00028 | 88 | 0.01601 | 20 |
| HLA-B*15:17, | 0.00273 | 34 | 0.00602 | 32 | 0.00453 | 40 | 0.00650 | 38 |
| HLA-B*35:01, | 0.05713 | 5 | 0.06494 | 3 | 0.04273 | 5 | 0.06353 | 1 |
| HLA-B*40:02, | 0.00991 | 20 | 0.00353 | 39 | 0.03056 | 14 | 0.04852 | 5 |
| HLA-B*44:02, | 0.09011 | 3 | 0.02116 | 17 | 0.00764 | 32 | 0.03327 | 9 |
| HLA-B*45:01, | 0.00426 | 28 | 0.04502 | 7 | 0.00226 | 52 | 0.01526 | 22 |
| HLA-A Sum |  | 0.04200 |  | 0.09859 |  | 0.00197 |  | 0.06978 |
| HLA-B Sum |  | 0.23157 |  | 0.21370 |  | 0.15845 |  | 0.21210 |

Based on the above calculations, it can therefore be expected that the AGGF1 cancer neoepitope will be present in about 49,757 patients and will be bound by an HLA type listed above in about 12,000 patients. Viewed form a different perspective, the AGGF1 cancer neoepitope may be effectively presented to a patient's immune system and with be at least potentially accessible as cancer specific target to a significant proportion of patients. Thus, the inventors also contemplate various compositions and methods that make use of the so presented cancer neoepitopes as further discussed in more detail below Encouraged by these results, the inventors also investigated whether or not distinct cancer subtypes would express and/or present cancer neoepitopes specific to the cancer subtype. For example, when looking at the breast cancer results, the inventors stratified the BRCA patient data sets into four distinct subsets following clinically relevant classifications: ER+ (estrogen receptor positive), PR+ (progesterone receptor positive), HER2+ (human epidermal growth factor receptor 2 positive), and triple negative (lacking ER, PR, and HER2) breast cancer.

Notably, Table 6 below shows exemplary results for common neoepitopes in triple negative breast cancer identified from a total of 35 samples. Here the frequency is shown as Repeat, the neoepitope sequence as mer (9-mer), while the affected gene is indicated along with the change in protein/type of mutation:

TABLE 6

| Repeats | Mer | Gene | PC |
|---|---|---|---|
| 4 | NRGLKKKKQ [SEQ ID NO: 4] | ['TAF1B'] | ['p.K63Kfs*6'] |
| 4 | LNRGLKKKK [SEQ ID NO: 5] | ['TAF1B'] | ['p.K63Kfs*6'] |
| 4 | RGLKKKKQY [SEQ ID NO: 6] | ['TAF1B'] | ['p.K63Kfs*6'] |
| 3 | TTLKLILVM [SEQ ID NO: 7] | ['RFC3'] | ['p.K79Kfs*27'] |
| 3 | GFVKAMINA [SEQ ID NO: 8] | ['SLC9A9'] | ['p.H190N'] |
| 3 | KKLKLAPLQ [SEQ ID NO: 9] | ['RFC3'] | ['p.K79Kfs*27'] |
| 3 | LILVMLEIV [SEQ ID NO: 10] | ['RFC3'] | ['p.K79Kfs*27'] |
| 3 | SSGAVSTRV [SEQ ID NO: 11] | ['KRTAP1-1'] | ['p.I116V'] |
| 3 | VRWCRPDCR [SEQ ID NO: 12] | ['KRTAP1-1'] | ['p.I116V'] |
| 3 | TPSKKKLKL [SEQ ID NO: 13] | ['RFC3'] | ['p.K79Kfs*27'] |
| 3 | DIAVTPLKL [SEQ ID NO: 14] | ['KMT2C'] | ['p.R380L'] |
| 3 | MHQQQQQQM [SEQ ID NO: 15] | ['PAXIP1'] | ['p.Q548del'] |
| 3 | PLQVTTTLK [SEQ ID NO: 16] | ['RFC3'] | ['p.K79Kfs*27'] |
| 3 | TTPSKKKLK [SEQ ID NO: 17] | ['RFC3'] | ['p.K79Kfs*27'] |
| 3 | ILVMLEIVT [SEQ ID NO: 18] | ['RFC3'] | ['p.K79Kfs*27'] |

TABLE 6-continued

| Repeats | Mer | Gene | PC |
|---|---|---|---|
| 3 | VSTRVRWCR [SEQ ID NO: 19] | ['KRTAP1-1'] | ['p.I116V'] |
| 3 | LKLAPLQVT [SEQ ID NO: 20] | ['RFC3'] | ['p.K79Kfs*27'] |
| 3 | KAMINAGQL [SEQ ID NO: 21] | ['SLC9A9'] | ['p.H190N'] |
| 3 | SCLPSCNNR [SEQ ID NO: 22] | ['FAM72B'] | ['p.G99R'] |
| 3 | KLAPLQVTT [SEQ ID NO: 23] | ['RFC3'] | ['p.K79Kfs*27'] |
| 3 | PSKKKLKLA [SEQ ID NO: 24] | ['RFC3'] | ['p.K79Kfs*27'] |
| 3 | NAGQLKNGD [SEQ ID NO: 25] | ['SLC9A9'] | ['p.H190N'] |
| 3 | HQQQQQQMQ [SEQ ID NO: 26] | ['PAXIP1'] | ['p.Q548del'] |
| 3 | LAGWQCPEC [SEQ ID NO: 27] | ['KMT2C'] | ['p.R380L'] |
| 3 | STRVRWCRP [SEQ ID NO: 28] | ['KRTAP1-1'] | ['p.I116V'] |

Similarly, Table 7 below shows exemplary results for common neoepitopes in ER+ breast cancer identified from a total of 43 samples. As above, the frequency is shown as Repeat, the neoepitope sequence as mer (9-mer).

TABLE 7

| Repeats | Mer | Gene |
|---|---|---|
| 11 | MKQMNDARH [SEQ ID NO: 29] | ['PIK3CA'] |
| 11 | RHGGWTTKM [SEQ ID NO: 30] | ['PIK3CA'] |
| 11 | ARHGGWTTK [SEQ ID NO: 31] | ['PIK3CA'] |
| 11 | QMNDARHGG [SEQ ID NO: 32] | ['PIK3CA'] |
| 11 | FMKQMNDAR [SEQ ID NO: 33] | ['PIK3CA'] |
| 11 | MNDARHGGW [SEQ ID NO: 34] | ['PIK3CA'] |
| 11 | KQMNDARHG [SEQ ID NO: 35] | ['PIK3CA'] |
| 11 | DARHGGWTT [SEQ ID NO: 36] | ['PIK3CA'] |
| 11 | NDARHGGWT [SEQ ID NO: 37] | ['PIK3CA'] |
| 4 | ASQIWNLNP [SEQ ID NO: 38] | ['USP8'] |
| 4 | SRLSASQIW [SEQ ID NO: 39] | ['USP8'] |
| 4 | SQIWNLNPV [SEQ ID NO: 40] | ['USP8'] |
| 4 | WNLNPVFGG [SEQ ID NO: 41] | ['USP8'] |
| 4 | RLSASQIWN [SEQ ID NO: 42] | ['USP8'] |
| 4 | IWNLNPVFG [SEQ ID NO: 43] | ['USP8'] |
| 4 | SASQIWNLN [SEQ ID NO: 44] | ['USP8'] |
| 4 | QIWNLNPVF [SEQ ID NO: 45] | ['USP8'] |
| 4 | LSASQIWNL [SEQ ID NO: 46] | ['USP8'] |
| 3 | IQPVLWTTP [SEQ ID NO: 47] | ['GATA3'] |
| 3 | FETESASVT [SEQ ID NO: 48] | ['AK097289'] |
| 3 | LWTTPPLQH [SEQ ID NO: 49] | ['GATA3'] |
| 3 | ALQPLQPHA [SEQ ID NO: 50] | ['GATA3'] |
| 3 | SASVTQAGV [SEQ ID NO: 51] | ['AK097289'] |
| 3 | LQPLQPHAD [SEQ ID NO: 52] | ['GATA3'] |
| 3 | ASVTQAGVQ [SEQ ID NO: 53] | ['AK097289'] |

Table 8 below shows exemplary results for common neoepitopes in PR+ breast cancer identified from a total of 33 samples. As before, the frequency is shown as Repeat, the neoepitope sequence as mer (9-mer), and the affected gene is listed.

TABLE 8

| Repeats | Mer | Gene |
|---|---|---|
| 10 | QMNDARHGG [SEQ ID NO: 54] | ['PIK3CA'] |
| 10 | ARHGGWTTK [SEQ ID NO: 55] | ['PIK3CA'] |
| 10 | FMKQMNDAR [SEQ ID NO: 56] | ['PIK3CA'] |
| 10 | MKQMNDARH [SEQ ID NO: 57] | ['PIK3CA'] |
| 10 | DARHGGWTT [SEQ ID NO: 58] | ['PIK3CA'] |
| 10 | MNDARHGGW [SEQ ID NO: 59] | ['PIK3CA'] |
| 10 | KQMNDARHG [SEQ ID NO: 60] | ['PIK3CA'] |
| 10 | NDARHGGWT [SEQ ID NO: 61] | ['PIK3CA'] |
| 10 | RHGGWTTKM [SEQ ID NO: 62] | ['PIK3CA'] |
| 3 | FFETESASV [SEQ ID NO: 63] | ['AK097289'] |
| 3 | ETESASVTQ [SEQ ID NO: 64] | ['AK097289'] |
| 3 | SFFFFETES [SEQ ID NO: 65] | ['AK097289'] |
| 3 | TLCSFFFFE [SEQ ID NO: 66] | ['AK097289'] |
| 3 | FETESASVT [SEQ ID NO: 67] | ['AK097289'] |
| 3 | ASQIWNLNP [SEQ ID NO: 68] | ['USP8'] |
| 3 | QIWNLNPVF [SEQ ID NO: 69] | ['USP8'] |

TABLE 8-continued

| Repeats | Mer | | Gene |
|---|---|---|---|
| 3 | YLGSLQPLP | [SEQ ID NO: 70] | ['AK097289'] |
| 3 | SASVTQAGV | [SEQ ID NO: 71] | ['AK097289'] |
| 3 | TQAGVQWRY | [SEQ ID NO: 72] | ['AK097289'] |
| 3 | SRLSASQIW | [SEQ ID NO: 73] | ['USP8'] |
| 3 | RYLGSLQPL | [SEQ ID NO: 74] | ['AK097289'] |
| 3 | ASVTQAGVQ | [SEQ ID NO: 75] | ['AK097289'] |
| 3 | QTLCSFFFF | [SEQ ID NO: 76] | ['AK097289'] |
| 3 | SQIWNLNPV | [SEQ ID NO: 77] | ['USP8'] |
| 3 | WNLNPVFGG | [SEQ ID NO: 78] | ['USP8'] |

Likewise, Table 9 below shows exemplary results for common neoepitopes in HER2+ breast cancer identified from a total of 19 samples. As above, the frequency is shown as Repeat, the nenenitnne sequence as mer (9-mer) and the affected gene is listed.

TABLE 9

| Repeat | Mer | | Gene |
|---|---|---|---|
| 2 | LPASHPLFG | [SEQ ID NO: 79] | ['LILRB1'] |
| 2 | ITNNFGSVA | [SEQ ID NO: 80] | ['PANK3'] |
| 2 | LVTITNNFG | [SEQ ID NO: 81] | ['PANK3'] |
| 2 | GPLPASHPL | [SEQ ID NO: 82] | ['LILRB1'] |
| 2 | LVTSQESGQ | [SEQ ID NO: 83] | ['FANCD2'] |
| 2 | VTITNNFGS | [SEQ ID NO: 84] | ['PANK3'] |
| 2 | TLVTITNNF | [SEQ ID NO: 85] | ['PANK3'] |
| 2 | TNNFGSVAR | [SEQ ID NO: 86] | ['PANK3'] |
| 2 | LLPGPLPAS | [SEQ ID NO: 87] | ['LILRB1'] |
| 2 | GGLVTSQES | [SEQ ID NO: 88] | ['FANCD2'] |
| 2 | TKQEKDFLW | [SEQ ID NO: 89] | ['PIK3CA'] |
| 2 | ATCSHYTQL | [SEQ ID NO: 90] | ['CLEC18B'] |
| 2 | FAKDGGLVT | [SEQ ID NO: 91] | ['FANCD2'] |
| 2 | KQEKDFLWS | [SEQ ID NO: 92] | ['PIK3CA'] |
| 2 | DPLSEITKQ | [SEQ ID NO: 93] | ['PIK3CA'] |
| 2 | ECARNATCS | [SEQ ID NO: 94] | ['CLEC18B'] |
| 2 | PASHPLFGR | [SEQ ID NO: 95] | ['LILRB1'] |

TABLE 9-continued

| Repeat | Mer | | Gene |
|---|---|---|---|
| 2 | FGSVARMCA | [SEQ ID NO: 96] | ['PANK3'] |
| 2 | EITKQEKDF | [SEQ ID NO: 97] | ['PIK3CA'] |
| 2 | ITKQEKDFL | [SEQ ID NO: 98] | ['PIK3CA'] |
| 2 | LSEITKQEK | [SEQ ID NO: 99] | ['PIK3CA'] |
| 2 | RNATCSHYT | [SEQ ID NO: 100] | ['CLEC18B'] |
| 2 | SEITKQEKD | [SEQ ID NO: 101] | ['PIK3CA'] |
| 2 | AKDGGLVTS | [SEQ ID NO: 102] | ['FANCD2'] |
| 2 | LPGPLPASH | [SEQ ID NO: 103] | ['LILRB1'] |

Therefore, it should be recognized that despite the fairly large number of individual neoepitopes in each cancer, several shared neoepitopes were nevertheless identified. Moreover, as can also be taken from the data in Tables 3 and 6-9, the neoepitopes affected the same gene, and in most cases even the same position. In addition, it should be noted that the above neoepitopes are not reflective of a change in sequence relative to a reference sequence from a healthy human, but are reflective of a change in sequence in the tumor of a patient relative to a healthy control sequence from the same patient.

Consequently, it should be appreciated that despite the apparent vast diversity of cancer neoepitopes, there are selected neoepitope sequences that are common among various cancer types as shown in Table 3 and that are common among different cancer subtypes as can be seen from Tables 3-6. Interestingly, some of the neoepitopes that were present in one subtype were also present in another subtype and may as such serve as a common marker for diagnosis and/or treatment.

Where common neoepitopes were not known or available, the inventors also used an approach similar to the methods discussed above to identify from whole genome sequencing data of tumor and matched normal patient samples a plurality of cancer neoepitopes. The same omics information was also used to predict the HLA-type, and after filtering for the expression levels and subtracting epitopes occurring in healthy tissue, the calculated neoepitopes were subjected to an in silico binding analysis to determine binding of the neoepitopes to the HLA. More particularly, 108 unique neoepitopes in a total of 108 neoepitopes were identified in an LA tumor with a total of 12 coding variants. The patient tumor was predicted to have HLA-A 24:02, HLA-B15:53, and HLA-DRB1 15:28. In silico HLA binding analysis (e.g., using netMEIC) and there was a HLA super type match with HLA-B*15:01, with 4 amino acid difference from patient's predicted allele HLA-B*15:53, and no matches were found to HLA-A*24:02 as is shown in the exemplary data of Table 10 below. Strong binding is typically predicted for calculated values of <50 nM, and weak binding for calculated values of <500 nM.

TABLE 10

| Gene | Mer | Binding Affinity (nM) | HLA |
|---|---|---|---|
| OXER1 | LTAIALNCY [SEQ ID NO: 104] | 141 | HLA-B15:01 |
| OXER1 | IALNCYLKV [SEQ ID NO: 105] | 384 | HLA-B15:03 |
| UTP20 | QKKRKALEF [SEQ ID NO: 106] | 10 | HLA-B15:03 |
| MRPL55 | ICYREPRRM [SEQ ID NO: 107] | 460 | HLA-B15:03 |
| PDZD8 | VFLGEMVPF [SEQ ID NO: 108] | 170 | HLA-B15:03 |

As can be readily seen from the above, computational analysis of multiple omics data for tumor-matched normal data sets allows for identification of neoepitopes that may be common or shared between different cancers and even different cancer subtypes. Moreover, when taken together with computational analysis of HLA-binding, neoepitope targets can be identified that may serve as immunological targets using various affinity molecules. Consequently, it should be appreciated that neoepitopes as identified herein can be used for various compositions and methods suitable for immunotherapy, either directly as immunogenic peptides used for vaccination (e.g., in association with a carrier), or indirectly as targets for molecules that specifically bind to the identified neoepitopes. For example, antibodies may be raised against the neoepitopes and so prepared antibodies may be used as cancer and neoepitope-specific targeting moiety. Of course, it should be appreciated that the antibodies may be full length immunoglobulins, fragments thereof, or synthetic antibodies or scFvs, or may even be part of a chimeric molecule (e.g., chimeric T-cell receptor).

Therefore, the inventors also contemplate a method of directing an agent to a cancer cell in which the cancer cell is contacted with an antibody or fragment thereof that binds to a cancer neoepitope as presented herein. For example, the neoepitope may be located in AGGF1, and may be formed by a V202L mutation in the AGGF1 protein. Therefore, suitable cancer epitopes especially include those having a sequence of SEQ ID NO:1, SEQ ID NO:2, or SEQ ID NO:3. Most typically, cancer cells found with such neoepitopes include various cancer cells such as BRCA (breast cancer) cells, CESC (cervical squamous cell carcinoma) cells, HNSC (head and neck squamous cell carcinoma) cells, LIHC (liver hepatocellular carcinoma) cells, LUAD (lung adenocarcinoma) cells, LUSC (lung squamous cell carcinoma) cells, OV (ovarian cancer) cells, READ (renal adenocarcinoma) cells, STAD (stomach adenocarcinoma) cells, THCA (thyroid carcinoma) cells, or UCEC (uterine corpus endometrioid carcinoma) cells.

On the other hand, where the cancer cell is a breast cancer cell, suitable neoepitopes will have a sequence of any one of SEQ ID NO:4 to SEQ ID NO:103. For example, for triple negative breast cancer cells, contemplated neoepitopes have a sequence of any one of SEQ ID NO:4 to SEQ ID NO:28, and for ER positive breast cancer cells, the neoepitope have a sequence of any one of SEQ ID NO:29 to SEQ ID NO:53. On the other hand, where the cancer cells are PR positive breast cancer cells, the neoepitope has a sequence of any one of SEQ ID NO:54 to SEQ ID NO:78, and where the cancer cells are HER2 positive breast cancer cells, the neoepitope has a sequence of any one of SEQ ID NO:79 to SEQ ID NO:103. Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified, thus fulfilling the written description of all Markush groups used in the appended claims.

With respect to suitable antibodies or antibody fragments it should be noted that the antibodies or fragments thereof may be generated in numerous manners well known in the art. Therefore, it should be appreciated that the antibodies or fragments may be synthetic or obtained via immunization of a mammal using one or more of the identified neoepitopes. Consequently, contemplated antibodies or fragments thereof may comprises IgG antibodies, a Fab, a F(ab')$_2$, or a scFv. Viewed from a different perspective, the inventors contemplate an antibody or fragment thereof that binds to a cancer neoepitope having a sequence of any one of SEQ ID NO:4 to SEQ ID NO:103. Therefore, it should be appreciated that the inventors contemplate the use of an antibody or fragment thereof to direct a diagnostic or therapeutic agent to a cancer cell, wherein the antibody or fragment thereof binds to a cancer neoepitope having a sequence of any one of SEQ ID NO:4 to SEQ ID NO:103. Where generation of an antibody is not desired, it is also contemplated that antibody libraries can be searched for one or more antibodies that bind to the neoantigen.

Of course, it should also be appreciated that the antibody or fragment thereof may be coupled to a therapeutic agent, a radiologic agent, and/or an imaging agent. For example, contemplated therapeutic agents include various chemotherapeutic drugs to so deliver the chemotherapeutic drug directly to a cancer cell. On the other hand, a radiologic agent may be coupled to the antibody or fragment thereof to selectively destroy a cancer cell and suitable radiologic agents include all agents suitable for brachytherapy, and especially $^{125}$I, $^{103}$Pd, or $^{192}$Ir. Alternatively, boron-10 may be used where neutron capture therapy with low-energy thermal neutrons is desired. Likewise, imaging agents may be coupled to the antibody or fragment thereof, and especially preferred imaging agents include PET (e.g., $^{11}$C, $^{13}$N, $^{15}$O, and $^{18}$F) and SPECT labels (e.g., $^{123}$I, $^{99m}$Tc, $^{133}$Xe, $^{201}$Tl, and $^{18}$F). As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Where the neoepitopes are employed in immune cell targeting, it should be noted that the antibody or fragment thereof may also be coupled to a portion of a T-cell receptor or a cytotoxic T-cell or an NK cell. Most preferably, where the antibody or fragment thereof is used in a chimeric T-cell receptor of a cytotoxic T-cell, the antigen binding portion of the chimeric T-cell receptor may have a scFv as ectodomain where the scFv has binding affinity against one of the neoepitopes of SEA ID NO:4-SEQ ID NO:103. On the other hand, where the antibody or fragment thereof is used with an NK cell, especially preferred NK cells are NK-92 derivatives that are modified to have a reduced or abolished expression of at least one killer cell immunoglobulin-like receptor (KIR), which will render such cells constitutively activated (via lack of or reduced inhibition). For example, such NK cells may be obtained from NantKwest (see nantkwest.com) as aNK cells (activated natural killer cells) and may then be further modified to express a membrane bound antibody or fragment thereof with binding affinity to any one of the neoepitopes of SEA ID NO:4-SEQ ID NO:103.

Alternatively, the NK cell may also be a NK-92 derivative that is modified to express the high-affinity Fcγ receptor (CD16), and it is especially contemplated that the antibodies contemplated herein may be bound to such modified NK cells. Such cells may be obtained from NantKwest as haNK cells (high-affinity natural killer cells). Likewise, the NK cell may also be genetically engineered to express a chimeric T-cell receptor. In especially preferred aspects, the chimeric T-cell receptor will have an scFv portion or other ectodomain with binding specificity against any one of the neoepitopes of SEA ID NO:4-SEQ ID NO:103.

Depending on the particular composition, it should therefore be appreciated that the step of contacting the cancer cell may be performed in vitro, in a non-patient mammal, or in the patient. For example, where the antibody of fragment thereof is used in diagnosis, the step of contacting may include binding the antibody of fragment thereof to a tissue sample ex vivo. (e.g., on a microscope slide to a FFPE sample) On the other hand, where binding efficacy is tested in vitro, the antibody of fragment thereof may be added to a tissue culture of a patient tumor. In still other uses, the antibody of fragment thereof may be administered to a patient in need thereof to provide a therapeutic, radiologic, or diagnostic agent to the cancer cell in vivo.

In further contemplated examples, the above noted neoepitopes are also suitable as immunostimulatory peptides, which may be administered to a mammal (and especially a patient) in form of an immunostimulatory composition. For example, the inventors contemplate an immunologic composition comprising a carrier to which is coupled a peptide having a sequence of any one of SEQ ID NO:4 to SEQ ID NO:28, of any one of SEQ ID NO:29 to SEQ ID NO:53, of any one of SEQ ID NO:54 to SEQ ID NO:78, or of any one of SEQ ID NO:79 to SEQ ID NO:103, and wherein the composition is formulated as a vaccine. Of course, it should be appreciated that such immunostimulatory peptides may comprise additional peptide portions that may be identical or different. For example, contemplated immunostimulatory peptides may comprise multiple neoantigens that may be separated by spacers (preferably flexible linkers such as GS4 linkers, etc.), typically comprising between 2 and 10 neoantigens. Use of such immunostimulatory composition may be prophylactically to provide a preventive protective immunity to a patient, or therapeutically to elicit an immune response to the neoepitopes, which is expected to translate to a therapeutic immune response against the tumor having such neoepitopes. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Moreover, it should be noted that the neoantigens presented herein may be further modified to improve binding affinity to a specific HLA-type, and particularly preferred positions for modification of the neoepitope sequence are at the termini. Consequently, the length of a neoepitope may vary. However, generally preferred that the length is between 8 and 11 amino acids (e.g., 9 mers), particularly where they are intended for MHC-I presentation. For MHC-II presentation, the neoepitope sequences presented herein may be extended to an overall length of between about 15-25 amino acids. Thus, modified neoepitopes are also specifically contemplated that will have a sequence identity of less than 100% as compared any one of SEQ ID NO: 1-103. For example, identity may be between 90-100%, or between 85-95%, or between 80-90%, or between 70-80%, or even less.

In yet further examples, the neoepitopes may also be expressed in a host cell (and typically a patient cell) form a recombinant nucleic acid, and all recombinant nucleic acids for such purpose are deemed suitable for use herein. Therefore, suitable recombinant nucleic acids will include a promoter sequence that is operably coupled to a nucleic acid sequence that encodes a protein having a sequence of any one of SEQ ID NO:4 to SEQ ID NO:103. Of course, it should be appreciated that the recombinant nucleic acid may comprise more than one sequence that encodes a neoepitope presented herein, and suitable recombinant nucleic acids will include at least two, three, four, five, or more sequence portions that encode the same or different neoepitopes. For example, suitable recombinant nucleic acids include expression vectors, and especially bacterial and viral expression vectors. However, naked DNA or linear DNA is also contemplated, particularly where the recombinant nucleic acid is used as a DNA vaccine. Thus, it should also be noted that where neoepitopes are expressed form a recombinant nucleic acid, that neoepitope is expressed in and presented on cells other than tumor cells, which is also a reflection of the recombinant nature of the so modified cell. Viewed from another perspective, the neoepitope outside the context of a cancer cell is a purely man-made, albeit in vivo, construct that would otherwise not occur.

Where recombinant viruses are employed, it is contemplated that all known manners of making recombinant viruses are deemed suitable for use herein, however, especially preferred viruses are those already established in gene therapy, including adenoviruses, adeno-associated viruses, alphaviruses, herpes viruses, lentiviruses, etc. However, among other appropriate choices, adenoviruses are particularly preferred. Moreover, it is further generally preferred that the virus is a replication deficient and non-immunogenic virus, which is typically accomplished by targeted deletion of selected viral proteins (e.g., E1, E3 proteins). Such desirable properties may be further enhanced by deleting E2b gene function, and high titers of recombinant viruses can be achieved using genetically modified human 293 cells as has been recently reported (e.g., *J Virol.* 1998 February; 72(2): 926-933). Most typically, the desired nucleic acid sequences (for expression from virus infected cells) are under the control of appropriate regulatory elements well known in the art.

With respect to the 'payload' of the genetically modified (adeno)virus it is contemplated that expression of more than one neoepitope is preferred, for example two, three, four, five, and even more, which can be accomplished using multiple distinct modified viruses, or a virus having more than one neoepitope sequence (e.g., as concatemeric or chimeric sequence). While not limiting to the inventive subject matter, it is generally preferred that neoepitope sequences are configured as a tandem minigene (e.g., $aa_{12}$-neoepitope$_{12}$-aa$_{12}$), or as single transcriptional unit, which may or may not be translated to a chimeric protein. Thus, it should be appreciated that the epitopes can be presented as monomers, multimers, individually or concatemeric, or as hybrid sequences with N- and/or C-terminal peptides. Most typically, it is preferred that the nucleic acid sequence is back-translated using suitable codon usage to accommodate the virus and/or host codon preference. However, alternate codon usage or non-matched codon usage is also deemed appropriate.

Viruses may then be individually or in combination used as a therapeutic vaccine in a pharmaceutical composition, typically formulated as a sterile injectable composition with a virus titer of between $10^4$-$10^{11}$ virus particles per dosage unit. However, alternative formulations are also deemed suitable for use herein, and all known routes and modes of administration are contemplated herein. As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.).

Lastly, it should be noted that where the virus comprises a nucleic acid payload that encodes multiple neoepitopes, it is contemplated that multiple neoepitopes may at least additively or synergistically enhance the host immune response. Similarly, where multiple viruses are used with each virus having a different neoepitope, it is contemplated that multiple neoepitopes may at least additively or synergistically enhance the host immune response. Such additive or synergistic effect may be genuine to a specific tumor or stage, or specific to particular patient parameter (e.g., age, gender, previous treatment, etc.)

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Moreover, all methods described herein can be performed in any suitable order unless otherwise indicated herein or otherwise clearly contradicted by context.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc. Lastly, The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

SEQUENCE LISTING

```
Sequence total quantity: 108
SEQ ID NO: 1            moltype = AA  length = 9
FEATURE                 Location/Qualifiers
source                  1..9
                        mol_type = protein
                        organism = Homo sapiens
SEQUENCE: 1
AEAALSQTG                                                                9

SEQ ID NO: 2            moltype = AA  length = 9
FEATURE                 Location/Qualifiers
source                  1..9
                        mol_type = protein
                        organism = Homo sapiens
SEQUENCE: 2
ALSQTGFSY                                                                9

SEQ ID NO: 3            moltype = AA  length = 9
FEATURE                 Location/Qualifiers
source                  1..9
                        mol_type = protein
                        organism = Homo sapiens
SEQUENCE: 3
EAALSQTGF                                                                9

SEQ ID NO: 4            moltype = AA  length = 9
FEATURE                 Location/Qualifiers
source                  1..9
```

```
                        mol_type = protein
                        organism = Homo sapiens
SEQUENCE: 4
NRGLKKKKQ                                                               9

SEQ ID NO: 5            moltype = AA   length = 9
FEATURE                 Location/Qualifiers
source                  1..9
                        mol_type = protein
                        organism = Homo sapiens
SEQUENCE: 5
LNRGLKKKK                                                               9

SEQ ID NO: 6            moltype = AA   length = 9
FEATURE                 Location/Qualifiers
source                  1..9
                        mol_type = protein
                        organism = Homo sapiens
SEQUENCE: 6
RGLKKKKQY                                                               9

SEQ ID NO: 7            moltype = AA   length = 9
FEATURE                 Location/Qualifiers
source                  1..9
                        mol_type = protein
                        organism = Homo sapiens
SEQUENCE: 7
TTLKLILVM                                                               9

SEQ ID NO: 8            moltype = AA   length = 9
FEATURE                 Location/Qualifiers
source                  1..9
                        mol_type = protein
                        organism = Homo sapiens
SEQUENCE: 8
GFVKAMINA                                                               9

SEQ ID NO: 9            moltype = AA   length = 9
FEATURE                 Location/Qualifiers
source                  1..9
                        mol_type = protein
                        organism = Homo sapiens
SEQUENCE: 9
KKLKLAPLQ                                                               9

SEQ ID NO: 10           moltype = AA   length = 9
FEATURE                 Location/Qualifiers
source                  1..9
                        mol_type = protein
                        organism = Homo sapiens
SEQUENCE: 10
LILVMLEIV                                                               9

SEQ ID NO: 11           moltype = AA   length = 9
FEATURE                 Location/Qualifiers
source                  1..9
                        mol_type = protein
                        organism = Homo sapiens
SEQUENCE: 11
SSGAVSTRV                                                               9

SEQ ID NO: 12           moltype = AA   length = 9
FEATURE                 Location/Qualifiers
source                  1..9
                        mol_type = protein
                        organism = Homo sapiens
SEQUENCE: 12
VRWCRPDCR                                                               9

SEQ ID NO: 13           moltype = AA   length = 9
FEATURE                 Location/Qualifiers
source                  1..9
                        mol_type = protein
                        organism = Homo sapiens
SEQUENCE: 13
TPSKKKLKL                                                               9

SEQ ID NO: 14           moltype = AA   length = 9
FEATURE                 Location/Qualifiers
```

```
source                  1..9
                        mol_type = protein
                        organism = Homo sapiens
SEQUENCE: 14
DIAVTPLKL                                                                9

SEQ ID NO: 15           moltype = AA   length = 9
FEATURE                 Location/Qualifiers
source                  1..9
                        mol_type = protein
                        organism = Homo sapiens
SEQUENCE: 15
MHQQQQQQM                                                                9

SEQ ID NO: 16           moltype = AA   length = 9
FEATURE                 Location/Qualifiers
source                  1..9
                        mol_type = protein
                        organism = Homo sapiens
SEQUENCE: 16
PLQVTTTLK                                                                9

SEQ ID NO: 17           moltype = AA   length = 9
FEATURE                 Location/Qualifiers
source                  1..9
                        mol_type = protein
                        organism = Homo sapiens
SEQUENCE: 17
TTPSKKKLK                                                                9

SEQ ID NO: 18           moltype = AA   length = 9
FEATURE                 Location/Qualifiers
source                  1..9
                        mol_type = protein
                        organism = Homo sapiens
SEQUENCE: 18
ILVMLEIVT                                                                9

SEQ ID NO: 19           moltype = AA   length = 9
FEATURE                 Location/Qualifiers
source                  1..9
                        mol_type = protein
                        organism = Homo sapiens
SEQUENCE: 19
VSTRVRWCR                                                                9

SEQ ID NO: 20           moltype = AA   length = 9
FEATURE                 Location/Qualifiers
source                  1..9
                        mol_type = protein
                        organism = Homo sapiens
SEQUENCE: 20
LKLAPLQVT                                                                9

SEQ ID NO: 21           moltype = AA   length = 9
FEATURE                 Location/Qualifiers
source                  1..9
                        mol_type = protein
                        organism = Homo sapiens
SEQUENCE: 21
KAMINAGQL                                                                9

SEQ ID NO: 22           moltype = AA   length = 9
FEATURE                 Location/Qualifiers
source                  1..9
                        mol_type = protein
                        organism = Homo sapiens
SEQUENCE: 22
SCLPSCNNR                                                                9

SEQ ID NO: 23           moltype = AA   length = 9
FEATURE                 Location/Qualifiers
source                  1..9
                        mol_type = protein
                        organism = Homo sapiens
SEQUENCE: 23
KLAPLQVTT                                                                9

SEQ ID NO: 24           moltype = AA   length = 9
```

```
FEATURE              Location/Qualifiers
source               1..9
                     mol_type = protein
                     organism = Homo sapiens
SEQUENCE: 24
PSKKKLKLA                                                           9

SEQ ID NO: 25        moltype = AA  length = 9
FEATURE              Location/Qualifiers
source               1..9
                     mol_type = protein
                     organism = Homo sapiens
SEQUENCE: 25
NAGQLKNGD                                                           9

SEQ ID NO: 26        moltype = AA  length = 9
FEATURE              Location/Qualifiers
source               1..9
                     mol_type = protein
                     organism = Homo sapiens
SEQUENCE: 26
HQQQQQQMQ                                                           9

SEQ ID NO: 27        moltype = AA  length = 9
FEATURE              Location/Qualifiers
source               1..9
                     mol_type = protein
                     organism = Homo sapiens
SEQUENCE: 27
LAGWQCPEC                                                           9

SEQ ID NO: 28        moltype = AA  length = 9
FEATURE              Location/Qualifiers
source               1..9
                     mol_type = protein
                     organism = Homo sapiens
SEQUENCE: 28
STRVRWCRP                                                           9

SEQ ID NO: 29        moltype = AA  length = 9
FEATURE              Location/Qualifiers
source               1..9
                     mol_type = protein
                     organism = Homo sapiens
SEQUENCE: 29
MKQMNDARH                                                           9

SEQ ID NO: 30        moltype = AA  length = 9
FEATURE              Location/Qualifiers
source               1..9
                     mol_type = protein
                     organism = Homo sapiens
SEQUENCE: 30
RHGGWTTKM                                                           9

SEQ ID NO: 31        moltype = AA  length = 9
FEATURE              Location/Qualifiers
source               1..9
                     mol_type = protein
                     organism = Homo sapiens
SEQUENCE: 31
ARHGGWTTK                                                           9

SEQ ID NO: 32        moltype = AA  length = 9
FEATURE              Location/Qualifiers
source               1..9
                     mol_type = protein
                     organism = Homo sapiens
SEQUENCE: 32
QMNDARHGG                                                           9

SEQ ID NO: 33        moltype = AA  length = 9
FEATURE              Location/Qualifiers
source               1..9
                     mol_type = protein
                     organism = Homo sapiens
SEQUENCE: 33
FMKQMNDAR                                                           9
```

-continued

| | | |
|---|---|---|
| SEQ ID NO: 34<br>FEATURE<br>source | moltype = AA   length = 9<br>Location/Qualifiers<br>1..9<br>mol_type = protein<br>organism = Homo sapiens | |
| SEQUENCE: 34<br>MNDARHGGW | | 9 |
| SEQ ID NO: 35<br>FEATURE<br>source | moltype = AA   length = 9<br>Location/Qualifiers<br>1..9<br>mol_type = protein<br>organism = Homo sapiens | |
| SEQUENCE: 35<br>KQMNDARHG | | 9 |
| SEQ ID NO: 36<br>FEATURE<br>source | moltype = AA   length = 9<br>Location/Qualifiers<br>1..9<br>mol_type = protein<br>organism = Homo sapiens | |
| SEQUENCE: 36<br>DARHGGWTT | | 9 |
| SEQ ID NO: 37<br>FEATURE<br>source | moltype = AA   length = 9<br>Location/Qualifiers<br>1..9<br>mol_type = protein<br>organism = Homo sapiens | |
| SEQUENCE: 37<br>NDARHGGWT | | 9 |
| SEQ ID NO: 38<br>FEATURE<br>source | moltype = AA   length = 9<br>Location/Qualifiers<br>1..9<br>mol_type = protein<br>organism = Homo sapiens | |
| SEQUENCE: 38<br>ASQIWNLNP | | 9 |
| SEQ ID NO: 39<br>FEATURE<br>source | moltype = AA   length = 9<br>Location/Qualifiers<br>1..9<br>mol_type = protein<br>organism = Homo sapiens | |
| SEQUENCE: 39<br>SRLSASQIW | | 9 |
| SEQ ID NO: 40<br>FEATURE<br>source | moltype = AA   length = 9<br>Location/Qualifiers<br>1..9<br>mol_type = protein<br>organism = Homo sapiens | |
| SEQUENCE: 40<br>SQIWNLNPV | | 9 |
| SEQ ID NO: 41<br>FEATURE<br>source | moltype = AA   length = 9<br>Location/Qualifiers<br>1..9<br>mol_type = protein<br>organism = Homo sapiens | |
| SEQUENCE: 41<br>WNLNPVFGG | | 9 |
| SEQ ID NO: 42<br>FEATURE<br>source | moltype = AA   length = 9<br>Location/Qualifiers<br>1..9<br>mol_type = protein<br>organism = Homo sapiens | |
| SEQUENCE: 42<br>RLSASQIWN | | 9 |
| SEQ ID NO: 43<br>FEATURE<br>source | moltype = AA   length = 9<br>Location/Qualifiers<br>1..9<br>mol_type = protein<br>organism = Homo sapiens | |
| SEQUENCE: 43<br>IWNLNPVFG | | 9 |

```
SEQ ID NO: 44           moltype = AA   length = 9
FEATURE                 Location/Qualifiers
source                  1..9
                        mol_type = protein
                        organism = Homo sapiens
SEQUENCE: 44
SASQIWNLN                                                                    9

SEQ ID NO: 45           moltype = AA   length = 9
FEATURE                 Location/Qualifiers
source                  1..9
                        mol_type = protein
                        organism = Homo sapiens
SEQUENCE: 45
QIWNLNPVF                                                                    9

SEQ ID NO: 46           moltype = AA   length = 9
FEATURE                 Location/Qualifiers
source                  1..9
                        mol_type = protein
                        organism = Homo sapiens
SEQUENCE: 46
LSASQIWNL                                                                    9

SEQ ID NO: 47           moltype = AA   length = 9
FEATURE                 Location/Qualifiers
source                  1..9
                        mol_type = protein
                        organism = Homo sapiens
SEQUENCE: 47
IQPVLWTTP                                                                    9

SEQ ID NO: 48           moltype = AA   length = 9
FEATURE                 Location/Qualifiers
source                  1..9
                        mol_type = protein
                        organism = Homo sapiens
SEQUENCE: 48
FETESASVT                                                                    9

SEQ ID NO: 49           moltype = AA   length = 9
FEATURE                 Location/Qualifiers
source                  1..9
                        mol_type = protein
                        organism = Homo sapiens
SEQUENCE: 49
LWTTPPLQH                                                                    9

SEQ ID NO: 50           moltype = AA   length = 9
FEATURE                 Location/Qualifiers
source                  1..9
                        mol_type = protein
                        organism = Homo sapiens
SEQUENCE: 50
ALQPLQPHA                                                                    9

SEQ ID NO: 51           moltype = AA   length = 9
FEATURE                 Location/Qualifiers
source                  1..9
                        mol_type = protein
                        organism = Homo sapiens
SEQUENCE: 51
SASVTQAGV                                                                    9

SEQ ID NO: 52           moltype = AA   length = 9
FEATURE                 Location/Qualifiers
source                  1..9
                        mol_type = protein
                        organism = Homo sapiens
SEQUENCE: 52
LQPLQPHAD                                                                    9

SEQ ID NO: 53           moltype = AA   length = 9
FEATURE                 Location/Qualifiers
source                  1..9
                        mol_type = protein
                        organism = Homo sapiens
SEQUENCE: 53
```

| | | |
|---|---|---|
| ASVTQAGVQ | | 9 |
| SEQ ID NO: 54<br>FEATURE<br>source<br><br>SEQUENCE: 54<br>QMNDARHGG | moltype = AA   length = 9<br>Location/Qualifiers<br>1..9<br>mol_type = protein<br>organism = Homo sapiens | <br><br><br><br><br>9 |
| SEQ ID NO: 55<br>FEATURE<br>source<br><br>SEQUENCE: 55<br>ARHGGWTTK | moltype = AA   length = 9<br>Location/Qualifiers<br>1..9<br>mol_type = protein<br>organism = Homo sapiens | <br><br><br><br><br>9 |
| SEQ ID NO: 56<br>FEATURE<br>source<br><br>SEQUENCE: 56<br>FMKQMNDAR | moltype = AA   length = 9<br>Location/Qualifiers<br>1..9<br>mol_type = protein<br>organism = Homo sapiens | <br><br><br><br><br>9 |
| SEQ ID NO: 57<br>FEATURE<br>source<br><br>SEQUENCE: 57<br>MKQMNDARH | moltype = AA   length = 9<br>Location/Qualifiers<br>1..9<br>mol_type = protein<br>organism = Homo sapiens | <br><br><br><br><br>9 |
| SEQ ID NO: 58<br>FEATURE<br>source<br><br>SEQUENCE: 58<br>DARHGGWTT | moltype = AA   length = 9<br>Location/Qualifiers<br>1..9<br>mol_type = protein<br>organism = Homo sapiens | <br><br><br><br><br>9 |
| SEQ ID NO: 59<br>FEATURE<br>source<br><br>SEQUENCE: 59<br>MNDARHGGW | moltype = AA   length = 9<br>Location/Qualifiers<br>1..9<br>mol_type = protein<br>organism = Homo sapiens | <br><br><br><br><br>9 |
| SEQ ID NO: 60<br>FEATURE<br>source<br><br>SEQUENCE: 60<br>KQMNDARHG | moltype = AA   length = 9<br>Location/Qualifiers<br>1..9<br>mol_type = protein<br>organism = Homo sapiens | <br><br><br><br><br>9 |
| SEQ ID NO: 61<br>FEATURE<br>source<br><br>SEQUENCE: 61<br>NDARHGGWT | moltype = AA   length = 9<br>Location/Qualifiers<br>1..9<br>mol_type = protein<br>organism = Homo sapiens | <br><br><br><br><br>9 |
| SEQ ID NO: 62<br>FEATURE<br>source<br><br>SEQUENCE: 62<br>RHGGWTTKM | moltype = AA   length = 9<br>Location/Qualifiers<br>1..9<br>mol_type = protein<br>organism = Homo sapiens | <br><br><br><br><br>9 |
| SEQ ID NO: 63<br>FEATURE<br>source | moltype = AA   length = 9<br>Location/Qualifiers<br>1..9<br>mol_type = protein<br>organism = Homo sapiens | |

```
SEQUENCE: 63
FFETESASV                                                                         9

SEQ ID NO: 64           moltype = AA  length = 9
FEATURE                 Location/Qualifiers
source                  1..9
                        mol_type = protein
                        organism = Homo sapiens
SEQUENCE: 64
ETESASVTQ                                                                         9

SEQ ID NO: 65           moltype = AA  length = 9
FEATURE                 Location/Qualifiers
source                  1..9
                        mol_type = protein
                        organism = Homo sapiens
SEQUENCE: 65
SFFFFETES                                                                         9

SEQ ID NO: 66           moltype = AA  length = 9
FEATURE                 Location/Qualifiers
source                  1..9
                        mol_type = protein
                        organism = Homo sapiens
SEQUENCE: 66
TLCSFFFFE                                                                         9

SEQ ID NO: 67           moltype = AA  length = 9
FEATURE                 Location/Qualifiers
source                  1..9
                        mol_type = protein
                        organism = Homo sapiens
SEQUENCE: 67
FETESASVT                                                                         9

SEQ ID NO: 68           moltype = AA  length = 9
FEATURE                 Location/Qualifiers
source                  1..9
                        mol_type = protein
                        organism = Homo sapiens
SEQUENCE: 68
ASQIWNLNP                                                                         9

SEQ ID NO: 69           moltype = AA  length = 9
FEATURE                 Location/Qualifiers
source                  1..9
                        mol_type = protein
                        organism = Homo sapiens
SEQUENCE: 69
QIWNLNPVF                                                                         9

SEQ ID NO: 70           moltype = AA  length = 9
FEATURE                 Location/Qualifiers
source                  1..9
                        mol_type = protein
                        organism = Homo sapiens
SEQUENCE: 70
YLGSLQPLP                                                                         9

SEQ ID NO: 71           moltype = AA  length = 9
FEATURE                 Location/Qualifiers
source                  1..9
                        mol_type = protein
                        organism = Homo sapiens
SEQUENCE: 71
SASVTQAGV                                                                         9

SEQ ID NO: 72           moltype = AA  length = 9
FEATURE                 Location/Qualifiers
source                  1..9
                        mol_type = protein
                        organism = Homo sapiens
SEQUENCE: 72
TQAGVQWRY                                                                         9

SEQ ID NO: 73           moltype = AA  length = 9
FEATURE                 Location/Qualifiers
source                  1..9
                        mol_type = protein
```

```
                              organism = Homo sapiens
SEQUENCE: 73
SRLSASQIW                                                                        9

SEQ ID NO: 74            moltype = AA   length = 9
FEATURE                  Location/Qualifiers
source                   1..9
                         mol_type = protein
                         organism = Homo sapiens
SEQUENCE: 74
RYLGSLQPL                                                                        9

SEQ ID NO: 75            moltype = AA   length = 9
FEATURE                  Location/Qualifiers
source                   1..9
                         mol_type = protein
                         organism = Homo sapiens
SEQUENCE: 75
ASVTQAGVQ                                                                        9

SEQ ID NO: 76            moltype = AA   length = 9
FEATURE                  Location/Qualifiers
source                   1..9
                         mol_type = protein
                         organism = Homo sapiens
SEQUENCE: 76
QTLCSFFFF                                                                        9

SEQ ID NO: 77            moltype = AA   length = 9
FEATURE                  Location/Qualifiers
source                   1..9
                         mol_type = protein
                         organism = Homo sapiens
SEQUENCE: 77
SQIWNLNPV                                                                        9

SEQ ID NO: 78            moltype = AA   length = 9
FEATURE                  Location/Qualifiers
source                   1..9
                         mol_type = protein
                         organism = Homo sapiens
SEQUENCE: 78
WNLNPVFGG                                                                        9

SEQ ID NO: 79            moltype = AA   length = 9
FEATURE                  Location/Qualifiers
source                   1..9
                         mol_type = protein
                         organism = Homo sapiens
SEQUENCE: 79
LPASHPLFG                                                                        9

SEQ ID NO: 80            moltype = AA   length = 9
FEATURE                  Location/Qualifiers
source                   1..9
                         mol_type = protein
                         organism = Homo sapiens
SEQUENCE: 80
ITNNFGSVA                                                                        9

SEQ ID NO: 81            moltype = AA   length = 9
FEATURE                  Location/Qualifiers
source                   1..9
                         mol_type = protein
                         organism = Homo sapiens
SEQUENCE: 81
LVTITNNFG                                                                        9

SEQ ID NO: 82            moltype = AA   length = 9
FEATURE                  Location/Qualifiers
source                   1..9
                         mol_type = protein
                         organism = Homo sapiens
SEQUENCE: 82
GPLPASHPL                                                                        9

SEQ ID NO: 83            moltype = AA   length = 9
FEATURE                  Location/Qualifiers
source                   1..9
```

| | | |
|---|---|---|
| | moltype = protein<br>organism = Homo sapiens | |
| SEQUENCE: 83<br>LVTSQESGQ | | 9 |
| SEQ ID NO: 84<br>FEATURE<br>source | moltype = AA length = 9<br>Location/Qualifiers<br>1..9<br>mol_type = protein<br>organism = Homo sapiens | |
| SEQUENCE: 84<br>VTITNNFGS | | 9 |
| SEQ ID NO: 85<br>FEATURE<br>source | moltype = AA length = 9<br>Location/Qualifiers<br>1..9<br>mol_type = protein<br>organism = Homo sapiens | |
| SEQUENCE: 85<br>TLVTITNNF | | 9 |
| SEQ ID NO: 86<br>FEATURE<br>source | moltype = AA length = 9<br>Location/Qualifiers<br>1..9<br>mol_type = protein<br>organism = Homo sapiens | |
| SEQUENCE: 86<br>TNNFGSVAR | | 9 |
| SEQ ID NO: 87<br>FEATURE<br>source | moltype = AA length = 9<br>Location/Qualifiers<br>1..9<br>mol_type = protein<br>organism = Homo sapiens | |
| SEQUENCE: 87<br>LLPGPLPAS | | 9 |
| SEQ ID NO: 88<br>FEATURE<br>source | moltype = AA length = 9<br>Location/Qualifiers<br>1..9<br>mol_type = protein<br>organism = Homo sapiens | |
| SEQUENCE: 88<br>GGLVTSQES | | 9 |
| SEQ ID NO: 89<br>FEATURE<br>source | moltype = AA length = 9<br>Location/Qualifiers<br>1..9<br>mol_type = protein<br>organism = Homo sapiens | |
| SEQUENCE: 89<br>TKQEKDFLW | | 9 |
| SEQ ID NO: 90<br>FEATURE<br>source | moltype = AA length = 9<br>Location/Qualifiers<br>1..9<br>mol_type = protein<br>organism = Homo sapiens | |
| SEQUENCE: 90<br>ATCSHYTQL | | 9 |
| SEQ ID NO: 91<br>FEATURE<br>source | moltype = AA length = 9<br>Location/Qualifiers<br>1..9<br>mol_type = protein<br>organism = Homo sapiens | |
| SEQUENCE: 91<br>FAKDGGLVT | | 9 |
| SEQ ID NO: 92<br>FEATURE<br>source | moltype = AA length = 9<br>Location/Qualifiers<br>1..9<br>mol_type = protein<br>organism = Homo sapiens | |
| SEQUENCE: 92<br>KQEKDFLWS | | 9 |
| SEQ ID NO: 93<br>FEATURE | moltype = AA length = 9<br>Location/Qualifiers | |

```
                          1..9
                          mol_type = protein
                          organism = Homo sapiens
SEQUENCE: 93
DPLSEITKQ                                                                      9

SEQ ID NO: 94             moltype = AA   length = 9
FEATURE                   Location/Qualifiers
source                    1..9
                          mol_type = protein
                          organism = Homo sapiens
SEQUENCE: 94
ECARNATCS                                                                      9

SEQ ID NO: 95             moltype = AA   length = 9
FEATURE                   Location/Qualifiers
source                    1..9
                          mol_type = protein
                          organism = Homo sapiens
SEQUENCE: 95
PASHPLFGR                                                                      9

SEQ ID NO: 96             moltype = AA   length = 9
FEATURE                   Location/Qualifiers
source                    1..9
                          mol_type = protein
                          organism = Homo sapiens
SEQUENCE: 96
FGSVARMCA                                                                      9

SEQ ID NO: 97             moltype = AA   length = 9
FEATURE                   Location/Qualifiers
source                    1..9
                          mol_type = protein
                          organism = Homo sapiens
SEQUENCE: 97
EITKQEKDF                                                                      9

SEQ ID NO: 98             moltype = AA   length = 9
FEATURE                   Location/Qualifiers
source                    1..9
                          mol_type = protein
                          organism = Homo sapiens
SEQUENCE: 98
ITKQEKDFL                                                                      9

SEQ ID NO: 99             moltype = AA   length = 9
FEATURE                   Location/Qualifiers
source                    1..9
                          mol_type = protein
                          organism = Homo sapiens
SEQUENCE: 99
LSEITKQEK                                                                      9

SEQ ID NO: 100            moltype = AA   length = 9
FEATURE                   Location/Qualifiers
source                    1..9
                          mol_type = protein
                          organism = Homo sapiens
SEQUENCE: 100
RNATCSHYT                                                                      9

SEQ ID NO: 101            moltype = AA   length = 9
FEATURE                   Location/Qualifiers
source                    1..9
                          mol_type = protein
                          organism = Homo sapiens
SEQUENCE: 101
SEITKQEKD                                                                      9

SEQ ID NO: 102            moltype = AA   length = 9
FEATURE                   Location/Qualifiers
source                    1..9
                          mol_type = protein
                          organism = Homo sapiens
SEQUENCE: 102
AKDGGLVTS                                                                      9

SEQ ID NO: 103            moltype = AA   length = 9
```

```
FEATURE             Location/Qualifiers
source              1..9
                    mol_type = protein
                    organism = Homo sapiens
SEQUENCE: 103
LPGPLPASH                                                                     9

SEQ ID NO: 104      moltype = AA  length = 9
FEATURE             Location/Qualifiers
source              1..9
                    mol_type = protein
                    organism = Homo sapiens
SEQUENCE: 104
LTAIALNCY                                                                     9

SEQ ID NO: 105      moltype = AA  length = 9
FEATURE             Location/Qualifiers
source              1..9
                    mol_type = protein
                    organism = Homo sapiens
SEQUENCE: 105
IALNCYLKV                                                                     9

SEQ ID NO: 106      moltype = AA  length = 9
FEATURE             Location/Qualifiers
source              1..9
                    mol_type = protein
                    organism = Homo sapiens
SEQUENCE: 106
QKKRKALEF                                                                     9

SEQ ID NO: 107      moltype = AA  length = 9
FEATURE             Location/Qualifiers
source              1..9
                    mol_type = protein
                    organism = Homo sapiens
SEQUENCE: 107
ICYREPRRM                                                                     9

SEQ ID NO: 108      moltype = AA  length = 9
FEATURE             Location/Qualifiers
source              1..9
                    mol_type = protein
                    organism = Homo sapiens
SEQUENCE: 108
VFLGEMVPF                                                                     9
```

The invention claimed is:

1. A method of producing an antibody and directing the antibody to a cancer cell expressing a neoepitope in human angiogenic factor with G patch and FHA domains 1 (AGGF1) protein, the method comprising:
producing an antibody by immunizing a mammal with a peptide consisting of SEQ ID NO: 1, SEQ ID NO:2, or SEQ ID NO:3, and isolating an antibody that binds to the peptide consisting of SEQ ID NO:1, SEQ ID NO:2, or SEQ ID NO:3; and
contacting a cancer cell with the isolated antibody, wherein the neoepitope in the human AGGF1 protein comprises a V202L mutation.

2. The method of claim 1 wherein the cancer cell is selected from the group consisting of a BRCA (breast cancer) cell, a CESC (cervical squamous cell carcinoma) cell, a HNSC (head and neck squamous cell carcinoma) cell, a LIHC (liver hepatocellular carcinoma) cell, a LUAD (lung adenocarcinoma) cell, a LUSC (lung squamous cell carcinoma) cell, an OV (ovarian cancer) cell, a READ (renal adenocarcinoma) cell, a STAD (stomach adenocarcinoma) cell, a THCA (thyroid carcinoma) cell, and a UCEC (uterine corpus endometrioid carcinoma) cell.

3. The method of claim 1 wherein the antibody further comprises a therapeutic agent.

4. The method of claim 1 wherein the antibody further comprises a radiologic agent.

5. The method of claim 1 wherein the antibody further comprises an imaging agent.

6. The method of claim 1 wherein the antibody is further coupled to a portion of a chimeric T-cell receptor of a cytotoxic T-cell or an NK cell.

7. The method of claim 1 wherein the antibody is further coupled to a cytotoxic T-cell or an NK cell.

8. The method of claim 1 wherein the step of contacting is performed in vivo.

9. A method of detecting a cancer cell, comprising:
producing an antibody by immunizing a mammal with a peptide consisting of SEQ ID NO: 1, SEQ ID NO:2, or SEQ ID NO:3, and isolating an antibody that binds to the peptide consisting of SEQ ID NO:1, SEQ ID NO:2, or SEQ ID NO:3;
contacting a cancer cell with the isolated antibody, wherein the cancer cell expresses a cancer neoepitope in AGGF1 (angiogenic factor with g-patch and FHA domains 1) protein;
wherein the cancer neoepitope is formed by a V202L mutation in the AGGF1 protein, and wherein the antibody comprises an imaging agent; and
detecting the imaging agent after the antibody or fragment thereof has bound to the cancer cell.

10. The method of claim 9 wherein the cancer cell is selected from the group consisting of a BRCA (breast cancer) cell, a CESC (cervical squamous cell carcinoma) cell, a HNSC (head and neck squamous cell carcinoma) cell, a LIHC (liver hepatocellular carcinoma) cell, a LUAD (lung adenocarcinoma) cell, a LUSC (lung squamous cell carcinoma) cell, an OV (ovarian cancer) cell, a READ (renal adenocarcinoma) cell, a STAD (stomach adenocarcinoma) cell, a THCA (thyroid carcinoma) cell, and a UCEC (uterine corpus endometrioid carcinoma) cell.

11. The method of claim 9 wherein the imaging agent comprises a PET label or a SPECT label.

12. A method of targeted treatment of a cancer cell, comprising:
producing an antibody by immunizing a mammal with a peptide consisting of SEQ ID NO: 1, SEQ ID NO:2, or SEQ ID NO:3, and isolating an antibody that binds to the peptide consisting of SEQ ID NO:1, SEQ ID NO:2, or SEQ ID NO:3;
contacting a cancer cell with the isolated antibody, wherein the cancer cell expresses a cancer neoepitope in AGGF1 (angiogenic factor with g-patch and FHA domains 1) protein;
wherein the cancer neoepitope is formed by a V202L mutation in the AGGF1 protein, and wherein the antibody comprises a therapeutic agent; and
allowing the antibody or fragment thereof to bind to the cancer cell to thereby effect targeted treatment of the cancer cell.

13. The method of claim 12 wherein the cancer cell is selected from the group consisting of a BRCA (breast cancer) cell, a CESC (cervical squamous cell carcinoma) cell, a HNSC (head and neck squamous cell carcinoma) cell, a LIHC (liver hepatocellular carcinoma) cell, a LUAD (lung adenocarcinoma) cell, a LUSC (lung squamous cell carcinoma) cell, an OV (ovarian cancer) cell, a READ (renal adenocarcinoma) cell, a STAD (stomach adenocarcinoma) cell, a THCA (thyroid carcinoma) cell, and a UCEC (uterine corpus endometrioid carcinoma) cell.

14. The method of claim 13 wherein the therapeutic agent comprises a chemotherapeutic drug, a radiologic agent, or a chimeric T-cell receptor of a cytotoxic T-cell or an NK cell.

* * * * *